United States Patent

Steiner et al.

[11] Patent Number: 5,475,105
[45] Date of Patent: Dec. 12, 1995

[54] N-SUBSTITUTED AZABICYCLOHEPTANE DERIVATIVES

[75] Inventors: Gerd Steiner, Kirchheim; Liiane Unger; Berthold Behl, both of Ludwigshafen; Hans-Juergen Teschendorf, Dudenhofen; Rainer Munschauer, Neustadt, all of Germany

[73] Assignee: BASF Aktiengesellschaft, Ludwigshafen, Germany

[21] Appl. No.: 356,178

[22] PCT Filed: Jun. 8, 1993

[86] PCT No.: PCT/EP93/01438

§ 371 Date: Dec. 16, 1994

§ 102(e) Date: Dec. 16, 1994

[87] PCT Pub. No.: WO94/00458

PCT Pub. Date: Jan. 6, 1994

[30] Foreign Application Priority Data

Jun. 19, 1992 [DE] Germany ............... 42 19 974.3
Dec. 21, 1992 [DE] Germany ............... 42 43 287.1

[51] Int. Cl.$^6$ ............. C07D 403/04; C07D 403/06; C07D 403/14; C07D 417/14
[52] U.S. Cl. ............ 544/48; 544/278; 544/279; 544/282; 544/285; 544/286; 544/287; 544/311; 544/312; 544/319; 544/320; 544/281; 548/305.1; 548/454; 548/455; 548/465
[58] Field of Search ............ 544/48, 278, 279, 544/282, 285, 286, 287, 311, 312, 319, 320, 281; 548/305.1, 454, 455, 465; 514/414

[56] References Cited

U.S. PATENT DOCUMENTS 4,540,318  9/1985  Hornung et al. ............... 408/9

FOREIGN PATENT DOCUMENTS

| 070053 | 1/1983 | European Pat. Off. |
| 100435 | 2/1984 | European Pat. Off. |
| 196132 | 10/1986 | European Pat. Off. |
| 921507 | 3/1963 | United Kingdom . |

OTHER PUBLICATIONS

Kenms, Chemical Abstract 102: 6522t (1985) for EP 110, 435 (Jun. 13, 1984).

Primary Examiner—Philip I. Datlow
Attorney, Agent, or Firm—Keil & Weinkauf

[57] ABSTRACT

Abstract of the Disclosure: Compounds of the formula I

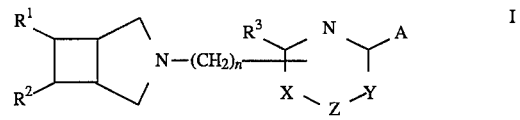

where $R^1, R^2, n, R^3, A, X, Y$ and $Z$ have the meanings stated in the description, and the preparation thereof are described. The novel compounds are suitable for controlling diseases, i.e., as neuroleptics, antidepressants, sedatives, hypnotics, CNS protectives or muscle relaxants.

1 Claim, No Drawings

N-SUBSTITUTED AZABICYCLOHEPTANE DERIVATIVES

The invention relates to novel N-substituted azabicycloheptane derivatives, the preparation and use thereof for preparing pharmaceutical agents.

It is known that 5- or 6-membered heterocyclic nitrogen derivatives with basic substituents have neuroleptic effects (EP 196 132, EP 70 053, EP 110 435).

It appears that the high affinities for serotonin receptors, in addition to the dopamine affinities, are particularly important for this.

We have now found that N-substituted 3-azabicyclo[3.2.0]heptane derivatives of the formula I

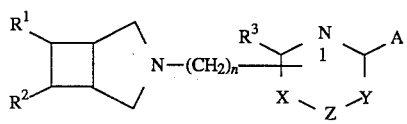

where
- $R^1$ is phenyl, pyridyl, thienyl or pyrrole [sic], each of which is unsubstituted or mono- or disubstituted by halogen, $C_1$–$C_4$-alkyl, trifluoromethyl, hydroxyl, $C_1$–$C_4$-alkoxy, amino, monomethylamino, dimethylamino, cyano or nitro,
- $R^2$ is hydrogen or phenyl which is unsubstituted or substituted by halogen, methoxy, hydroxyl or amino,
- n is 0, 1, 2, 3 or 4,
- $R^1$ is hydrogen, hydroxyl, $C_1$–$C_4$-alkyl or $C_1$–$C_4$-alkoxy, or together with the adjacent carbon atom is C=O or C=S,
- X and Y are each C, CH, $CH_2$, NH or $C_1$–$C_4$-alkyl-N or N,
- Z is a direct linkage, CO, CS or CH or $C_2$ in which one hydrogen can be replaced by hydroxyl, amino, $C_1$–$C_4$-alkoxy or halogen, and
- A is hydrogen, hydroxyl, amino, mercapto, $C_1$–$C_4$-alkylamino, di-$C_1$–$C_4$-alkylamino, $C_1$–$C_4$-alkylthio or $C_1$–$C_4$-alkoxy, or together with the adjacent carbon atom is C=O, or
- A is $C_3$–$C_4$-alkylene which is attached to Y and which can contain one or two non-cumulative double bonds and in which one CH or $CH_2$ can be replaced by N, S, NH or N-$CH_3$, and where the ring can be either mono-substituted by fluorine, chlorine, methyl, methoxy, nitro or amino or, in the case of a benzene ring, mono-, di- or trisubstituted by fluorine, chlorine, methyl, trifluoromethyl, nitro, hydroxyl, methoxy, amino, monomethylamino or dimethylamino, and in which the ring on the right in formula I can have $C_1$–$C_4$-alkyl, allyl or benzyl attached to N-1 and can contain 1–3 non-cumulative double bonds, and the salts thereof with physiologically tolerated acids have valuable pharmacological properties.

The following meanings may be particularly mentioned for $R^1$, $R^2$, $R^3$ and n:
- $R^1$: phenyl which is unsubstituted or substituted by fluorine, chlorine, iodine, methoxy, nitro, trifluoromethyl, hydroxyl or amino,
- $R^2$: hydrogen,
- $R^3$: methyl and hydroxyl,
- n: 2.

The ring system on the right in formula I is, in particular,

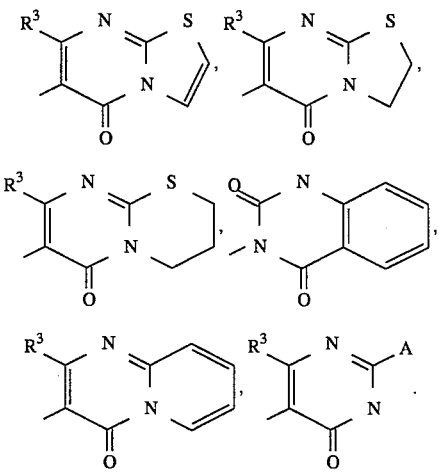

Particularly preferred compounds are those where
- $R^1$ is phenyl which is preferably substituted in the p position by fluorine and chlorine or in the m position by fluorine or chlorine
- $R^2$ is hydrogen and
- $R^3$ is methyl and hydroxyl and the ring system on the right in the molecule is derived from
- 7-methyl-5H-thiazolo[3,2-a]pyrimidin-5-one,
- 7-methyl-2,3-dihydro-5H-thiazolo[3,2-a]pyrimidin-5-one,
- 8-methyl-2H,6H-pyrimido[2,1-b][1,3]thiazin-6-one,
- 2,4(1H,3H)-quinazolinedione,
- 2-methyl-4H-pyrido[1,2-a]pyrimidin-4-one,
- 6,7,8,9-tetrahydro-2-methyl-4H-pyrido[1,2-a]pyrimidin-4-one or
- 2-methylamino-3,6-dimethyl-4(3H)-pyrimidinone.

The following compounds are particularly preferred:
- 6-β-[exo-6-p-fluorophenyl-3-azabicyclo[3.2.0]heptan-3-yl]-ethyl-7-methyl-5H-thiazolo[3,2-a]pyrimidin-5-one,
- 6-β-[exo-6-p-chlorophenyl-3-azabicyclo[3.2.0]heptan-3-yl]-ethyl-7-methyl-5H-thiazolo[3,2-a]pyrimidin-5-one,
- 6-β-[exo-6-p-fluorophenyl-3-azabicyclo[3.2.0]heptan-3-yl]-ethyl-7-methyl-2,3-dihydro-5H-thiazolo[3,2-a]-pyrimidin-5-one,
- 6-β-[exo-6-p-fluorophenyl-3-azabicyclo[3.2.0]heptan-3-yl]-ethyl-8-methyl-2H,6H-pyrimido[2,1-b][1,3]thiazin-6-one,
- 6-β-[exo-6-p-fluorophenyl-3-azabicyclo[3.2.0]heptan-3-yl]-ethyl-2,4-(1H,3H)-quinazolinedione,
- 3-β-[exo-6-p-trifluoromethylphenyl-3-azabicyclo[3.2.0]heptan-3-yl]-ethyl-2,4-(1H,3H)-quinazolinedione,
- 3-β-[exo-6-p-fluorophenyl-3-azabicyclo[3.2.0]heptan-3-yl]-ethyl-2-methyl-4H-pyrido-[1,2-a]pyrimidin-4-one,
- 3-β-[exo-6-p-fluorophenyl-3-azabicyclo[3.2.0]heptan-3-yl]-ethyl-6,7,8,9-tetrahydro-2-methyl-4H-pyrido[1,2-a]-pyrimidin-4-one,
- 5-β-[exo-6-p-fluorophenyl-3-azabicyclo[3.2.0]heptan-3-yl]-ethyl-2-methylamino-3,6-dimethyl-4(3H)-pyrimidinone,
- 5-β-[exo-6-m-chlorophenyl-3-azabicyclo[3.2.0]heptan-3-yl]ethyl-2-methylamino-3,6-dimethyl-4(3H)-pyrimidinone.

The compounds of the formula I according to the invention can be prepared by reacting a compound of the formula II

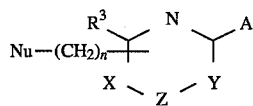

where n, $R^3$, X, Y, Z and A have the abovementioned meanings, and Nu is a nucleofugic leaving group, with a 3-azabicyclo[3.2.0]heptane derivative of the formula III

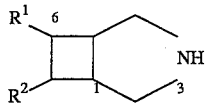

where $R^1$ and $R^2$ have the abovementioned meanings, and converting the resulting compound where appropriate into the addition salt with a physiologically tolerated acid.

Suitable and preferred for the nucleofugic leaving group Nu are halogens, especially bromine or chlorine.

The reaction is expediently carried out in the presence of an inert base such as triethylamine or potassium carbonate to bind the acid and in an inert solvent such as a cyclic saturated ether, especially tetrahydrofuran or dioxane, or an aromatic hydrocarbon such as toluene or xylene.

The reaction is usually carried out at from 20° to 150° C. in particular from 80° to 140° C., and is generally complete after from 1 to 10 hours.

The compounds of the formula I according to the invention can be purified either by recrystallization from conventional organic solvents, preferably from a lower alcohol such as ethanol, or by column chromatography.

Racemates can be resolved into the enantiomers in a straightforward way by classical methods using optically active carboxylic acids, eg. tartaric acid derivatives, in an inert solvent, eg. lower alcohols.

The free 3-azabicyclo[3.2.0]heptane derivatives of the formula I can be converted in a conventional way into the addition salt with a pharmacologically acceptable acid, preferably by adding one equivalent of the appropriate acid to a solution thereof. Examples of pharmaceutically acceptable acids are hydrochloric acid, phosphoric acid, sulfuric acid, methanesulfonic acid, sulfamic acid, maleic acid, fumaric acid, oxalic acid, tartaric acid or citric acid.

The compounds according to the invention have valuable pharmacological properties. They can be used as neuroleptics (especially atypical), antidepressants, sedatives, hypnotics, CNS protectives or muscle relaxants. It is possible for more than one of the said effects to occur together in a compound according to the invention. The pharmacological effects are demonstrated both in vivo and in vitro, and the substances can be characterized in particular by the affinity, which is in some cases very high and selective, for receptor subtypes such as dopamine $D_1$, $D_2$, $D_3$ and $D_4$ receptors, serotonin 1A, 1D and 2 receptors, alpha 1 and 2 receptors, histamine 1 and muscarine receptors.

The following methods are used for the in vivo characterization:

a) Influence on orientation motility

Mice in a new environment show exploratory behavior which is manifested by increased motor activity. This motor activity is measured in a cage with a photoelectric detector for 30 min after the animals (female NMRI mice) have been placed in the cage.

ED50: dose which reduces the motor activity by 50% from that of placebo-treated controls.

b) Apomorphine antagonism

Female NMRI mice receive 1.21 mg/kg apomorphine s.c. At this dose, apomorphine leads to motor activation which is manifested by continuous climbing when the animals are placed in wire mesh cages. The climbing is scored in the following way (every 2 min for 30 min):

0: animal has four paws on the floor

1: animal has two paws on the wire

2: animal has four paws on the wire (is climbing).

The climbing behavior is inhibited by pretreatment with antipsychotics.

ED50: dose which inhibits the climbing activity of the animals by 50% from that of placebo-treated controls.

c) Methamphetamine antagonism

Female NMRI mice receive 1 mg/kg methamphetamine orally and, after 30 min, are placed in a cage with a photoelectric detector to measure the motor activity (2 animals/cage, 4 cages/dose). The test substances are given orally 30 min before the methamphetamine. The increase in activity caused by methamphetamine for the period from 15 to 60 min after the animals are placed in the cage is calculated as the difference between methamphetamine controls and placebo controls and set equal to 100%. The ED100 is the dose of test substance which completely abolishes the increase in activity.

d) L-5-HTP antagonism

Female Sprague-Dawley rats receive L-5-HTP in a dose of 316 mg/kg i.p. The animals then develop an excitation state, and the following symptoms of this for paw treading and tremor are scored (0=absent, 1=moderate, 2=marked) every 10 min from 20 to 60 min after L-5-HTP administration. The average score after L-5-HTP administration is 17. The test substances are administered orally 60m in before L-5-HTP. The ED50 is the dosage which reduces the average score by 50% from that of the controls.

The stated methods are suitable for characterizing substances as antipsychotics; in particular, the inhibition of the methamphetamine-induced motor stimulation is regarded as predictive of an antipsychotic effect. Inhibition of the L-5-HTP excitation indicates a serotonin-antagonistic effect, which is characteristic of atypical neuroleptics.

The novel compounds show a good effect in these tests.

The present invention accordingly also relates to a therapeutic composition which has a content of a compound of the formula I or the pharmacologically acceptable acid addition salt thereof as active ingredient in addition to conventional excipients and diluents, as well as to the use of the novel compounds for controlling diseases.

The compounds according to the invention can be administered orally or parenterally, intravenously or intramuscularly, in a conventional way.

The dosage depends on the age, condition and weight of the patient and on the mode of administration. The daily dose of active ingredient is normally about 1–100 mg/kg of body weight on oral administration and 0.1–10 mg/kg of body weight on parenteral administration.

The novel compounds can be used in conventional solid or liquid pharmaceutical forms, eg. as uncoated or (film-)coated tablets, capsules, powders, granules, suppositories, solutions, ointments, creams or sprays. These are produced in a conventional way. The active ingredients can for this purpose be processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellent gases (cf. H. Sucker et al.: Pharmazeutische Technologie, Thieme-Verlag, Stuttgart, 1978). The forms obtained in this way normally contain from 1 to 99% by weight of the active ingredient.

The substances of the formula II which are required as starting materials for synthesizing the novel compounds are known or can be synthesized from appropriate starting materials by preparation methods described in the literature.

The substances of the formula III can be prepared by subjecting an amine of the formula

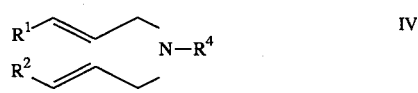

where $R^1$ and $R^2$ have the abovementioned meanings, and $R^4$ is hydrogen, acetyl, benzyl or trifluoroacetyl, to a photochemical 2+2 cycloaddition and, where appropriate, eliminating an acyl or benzyl group.

The photoreaction takes place satisfactorily in an inert solvent, preferably acetone, at from 20° to 80° C. A particularly suitable light source is a high-pressure mercury lamp. It is advantageous where appropriate to carry out the photocycloaddition in a silica apparatus under a nitrogen atmosphere with or without the addition of about 1 mol of hydrochloric acid per mol of amine.

In most cases, the photocycloaddition takes place highly diastereoselectively to give the bicyclic compounds III with $R^1$ and $R^2$ in the exo configuration:

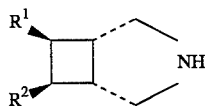

The two enantiomers can be isolated pure by racemate resolution, eg. using optically active tartaric acid derivatives.

An acyl group is eliminated by conventional methods, as is a benzyl group.

The amines of the formula IV are disclosed in the literature or can be prepared by either reacting an aldehyde $R^1$-CHO with vinylmagnesium chloride to give the allyl alcohol V

subsequently rearranging with hydrogen chloride to give the allyl chloride VI

and finally substituting with the appropriate allylamine VII

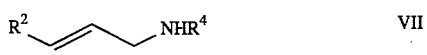

or subjecting a cinnamaldehyde VIII

directly to reductive amination with the allylamine VII where $R^4$ is hydrogen.

The following examples illustrate the invention:

A Preparation of the Starting Materials aa) 1-(4-Fluorophenyl)allyl alcohol 1550 ml (2.0M [sic]) of a 1.29M solution of vinylmagnesiumchloride in tetrahydrofuran were introduced under nitrogen to a 4 l stirred flask. Subsequently, while stirring under nitrogen, a solution of 222.0 g (1.764M [sic]) of 4-fluorobenzaldehyde in tetrahydrofuran was added at 30°–35° C. in the course of 30 min while cooling the mixture in ice. The mixture was then stirred at room temperature under nitrogen for 2.5 h. Subsequently, while stirring and cooling with ice, 180 ml of water were added, the mixture was filtered with suction, and the residue on the filter was washed three times with 150 ml of tetrahydrofuran. The filtrates were combined, dried with sodium sulfate and concentrated to yield 265.7 g (99%) of product as a yellowish brown oil.

ab) 3-(4-Fluorophenyl)allyl chloride 273.6 g (1.798M [sic]) of 1-(4-fluorophenyl)allyl alcohol were dissolved by stirring in 2000 ml of methanol. Subsequently, 101.0 g (2.770M [sic]) of hydrogen chloride were passed in over the course of 3 h, during which the temperature rose to 37° C. The mixture was then stirred for 1 h, washed with 600 ml of ice-cold water and a mixture of 150 ml of saturated brine and 150 ml of water and then dried over sodium sulfate and concentrated to yield 294.6 g (98%) of a brown oil.

ac) N-Allyl-N-[3-(4-fluorophenyl)allyl]amine 231.8 g (1.359M [sic]) of 3-(4-fluorophenyl)-allyl chloride were added over the course of 25 min to a refluxing solution of 795.0 g (13.92M [sic]) of allylamine in 360 ml of toluene, and then refluxing was continued for 1 h.

Subsequently, 1000 ml were distilled out through a 10 cm column (5 mm glass rings) with the bath at up to 125° C. 1000 ml of water were added to the residue, and the pH was adjusted to 0.7 with 38% strength hydrochloric acid. The organic phase was separated off and discarded. The aqueous phase was adjusted to pH 12.7 with 50% strength sodium hydroxide solution and was extracted with toluene and concentrated. The residue was distilled through a column under 0.7–1 mbar to yield, with the bath at 120°–160° C., 191.8 g (74%) of a pale yellow oil.

ad) exo-6-(p-Fluorophenyl)-3-azabicyclo[3.2.0]heptane 130 ml of 10% strength hydrochloric acid and 600 mg of Michler's ketone were added to 19.4 g (102 mM [sic]) of N-allyl-N-[3-(4-fluorophenyl)allyl]amine, and the mixture was exposed under nitrogen to a 150 watt high-pressure mercury lamp in a silica apparatus at room temperature for 55 h. The mixture was then evaporated and the residue was partitioned between methylene chloride and water. The aqueous phase was made alkaline with aqueous ammonia solution and extracted twice more with methylene chloride. The combined organic phases were dried with sodium sulfate and concentrated. Yield 19.3 g (99%), melting point: 165°–166° C. (maleate). The antipodes were separated by adding 15.0 g (78.5 mM [sic]) of the racemate to a solution of 31.7 g (78.5 mM [sic]) of (−)-di-O-toluoyl-L-tartaric acid in 300 ml of boiling ethanol. The crystals which separated out on cooling (13.8 g) were filtered off with suction, washing with ethanol and recrystallized from 200 ml of ethanol with the addition of 200 ml of water. Liberation of the base provided the (+) antipode (5.5 g) with $[\alpha]_D = +970°$ (EtOH, c=0.969). 14.2 g of salt crystallized out of the mother liquor overnight and were recrystallized from 400 ml of ethanol (insolubles filtered off at the boiling point and solution concentrated to 300 ml). Liberation of the base yielded 4.0 g of the (−) antipode with $[\alpha]_D$=−96.0°. EtOH, c=0.940). The exo-phenyl configurations were demonstrated by X-ray structural analysis.

ae) exo-6-Phenyl-3-azabicyclo[3.2.0]heptane 300 ml of 10% strength hydrochloric acid were added to 50.0 g (28.9 mM [sic]) of N-cinnamyl-N-allylamine in 1600 ml of acetone and the mixture was exposed under nitrogen to a 150 watt high-pressure mercury lamp in a silica apparatus at room temperature for 48 h. The mixture was then concentrated, and the residue was partitioned between methylene chloride and water. The aqueous solution was made alkaline with aqueous ammonia solution and then extracted twice more with methylene chloride. The combined organic phases were dried with sodium sulfate and concentrated. Yield 49.0 g (98%) of viscous oil, melting point 177°–178° C.(maleate).

af) exo-6,7-Diphenyl-3-azabicyclo[3.2.0]heptane 16.0 g (254 mM [sic]) of ammonium formate and 2.0 g of palladium (10%) on carbon were added to 12.0 g (35.4 mM [sic]) of exo-6,7-diphenyl- 3-benzyl-3-azabicyclo[3.2.0] heptane in a mixture of 300 ml of n-propanol and 16 ml of water, and the mixture was refluxed for 4 h (evolution of carbon dioxide). After cooling, the catalyst was filtered off by suction, washing with propanol and methylene chloride, and the filtrate was concentrated. The residue was partitioned between methylene chloride and water, and the aqueous phase was made alkaline with aqueous ammonia solution and extracted twice more with methylene chloride. The combined organic phases were dried with sodium sulfate and concentrated to yield 8.1 g (92%) of product, melting point 140°–142° C. (maleate).

ag) N-Allyl-N-3-(3,5-dichlorophenyl)allylamine 4.5 ml (60 mM [sic], 3.4 g) of allylamine and 17.0 g of sodium sulfate were added to 12.0 g (59.7 mM [sic]) of 3,5-dichlorocinnamaldehyde in 180 ml of methylene chloride, and the mixture was stirred at room temperature for 24 h. The sodium sulfate was then filtered off and washed with methylene chloride, and the filtrate was evaporated to dryness. The resulting yellow oil was dissolved in 200 ml of absolute methanol and, under nitrogen, 2.5 g (66.0 mM [sic]) of sodium borohydride were added a little at a time. The mixture became slightly warm and was then stirred for 1 h and subsequently neutralized (pH=7) with 10% strength hydrochloric acid. The solvent was removed under reduced pressure, and the residue was taken up in methylene chloride. The organic phase was washed twice with water, dried over sodium sulfate and concentrated. The residue was purified by column chromatography (silica gel, methylene chloride +5% methanol). Yield: 9.2 g (63%) of yellow oil.

ah) N-Allyl-N-[3-(3-pyridyl)allyl]-2,2,2-trifluoro-acetamide 16.1 g (76.6 mM [sic]) of trifluoroacetic anhydride were slowly added dropwise to a solution of 10.0 g (57.5 mM [sic]) of N-allyl-N-3-(3-pyridyl)allylamine and 10.7 ml of triethylamine in 100 ml of tetrahydrofuran at 0° C. The mixture was then stirred at room temperature for 2 h, poured into 250 ml of ice-water and extracted three times with 150 ml of methyl tert.-butyl ether each time. The combined organic phases were dried over sodium sulfate and concentrated. Yield: 14.3 g (92%) of dark brown oil.

ai) 2,2,2-Trifluoro-1-[exo-6-(3-pyridyl)-3-azabicyclo[3.2.0]hept-3-yl]ethanone 14.0 g (51.8 mM [sic]) of N-allyl-N-[3-(3-pyridyl)allyl]-2,2,2-trifluoroacetamide were dissolved in 140 ml of acetone, 30 ml of a 10% strength aqueous hydrochloric acid were added, and the mixture was exposed to a 150 watt high-pressure mercury lamp in a Duran glass apparatus at room temperature under nitrogen for 48 h. The solution was then concentrated, the residue was taken up in 150 ml of water, and the solution was adjusted to pH 8–9 with an aqueous ammonia solution. The aqueous phase was extracted twice with methyl tert.-butyl ether, and the combined organic phases were dried over sodium sulfate and concentrated. The residue was fractionated by column chromatography (silica gel, methylene chloride +2% methanol) to yield 6.2 g (42%) of unchanged N-allyl-N-[3-( 3-pyridyl)allyl]-2,2,2-trifluoroacetamide and 3.7 g (26%) of 2,2,2-trifluoro-1-[exo-6-(3-pyridyl)- 3-azabicyclo-[3.2.0]hept-3-yl]ethanone as dark oil.

ak) exo-6-(3-Pyridyl)-3-azabicyclo[3.2.0]heptane 2.5 g of potassiumhydroxide pellets were added to a solution of 3.7 g (13.7 mM [sic]) of 2,2,2-trifluoro-1-[exo-6-(3-pyridyl)-3-azabicyclo[ 3.2.0]hept-3-yl]ethanone in 50 ml of ethanol, and the solution was then stirred at room temperature for 2 h and subsequently poured into 100 ml of ice-water. The aqueous phase was extracted three times with methyl tert.-butyl ether, and the combined organic phases were dried over sodium sulfate and concentrated. Yield 2.3 g (96%) of yellow oil, melting point 202°–205° C. (hydrochloride). The following substances can be prepared in a similar way:

al) exo-6-(m-fluorophenyl)-3-azabicyclo[3.2.0]heptane
am) exo-6-(o-fluorophenyl)-3-azabicyclo[3.2.0]heptane, melting point 118°–120° C. (maleate)
an) exo-6-(p-chlorophenyl)-3-azabicyclo[3.2.0]heptane, melting point 152°–154° C. (maleate)
ao) exo-6-(m-chlorophenyl)-3-azabicyclo[3.2.0]heptane, melting point 130°–132° C. (maleate)
ap) exo-6-(p-methoxyphenyl)-3-azabicyclo[3.2.0]heptane
aq) exo-6-(m-methoxyphenyl)-3-azabicyclo[3.2.0]heptane
ar) exo-6-(p-nitrophenyl)-3-azabicyclo[3.2.0]heptane, melting point 158°–160° C. (maleate)
as) exo-6-(m-nitrophenyl)-3-azabicyclo[3.2.0]heptane
at) exo-6-(p-trifluoromethylphenyl)-3-azabicyclo[3.2.0]heptane, melting point 155°–156° C. (maleate)
au) exo-6-(m-trifluoromethylphenyl)-3-azabicyclo[3.2.0]heptane
av) exo-6-(3,4-dichlorophenyl)-3-azabicyclo[3.2.0]heptane
aw) exo-6-(3,5-dichlorophenyl)-3-azabicyclo[3.2.0]heptane, melting point >250° C. (hydrochloride)
ax) exo-6-(3,4-dimethoxyphenyl)-3-azabicyclo[3.2.0]heptane
ay) exo-6-(m-hydroxyphenyl)-3-azabicyclo[3.2.0]heptane
az) exo-6-(p-hydroxyphenyl)-3-azabicyclo[3.2.0]heptane
ba) exo-6-(3,4-dihydroxyphenyl)-3-azabicyclo[3.2.0]heptane
bb) exo-6-(p-methylphenyl)-3-azabicyclo[3.2.0]heptane
bc) exo-6-(m-methylphenyl)-3-azabicyclo[3.2.0]heptane
bd) exo-6-(p-t-butylphenyl)-3-azabicyclo[3.2.0]heptane, melting point >255° C. (hydrochloride)
be) exo-6-(m-aminophenyl)-3-azabicyclo[3.2.0]heptane
bf) exo-6-(p-aminophenyl)-3-azabicyclo[3.2.0]heptane
bg) exo-6-(p-cyanophenyl)-3-azabicyclo[3.2.0]heptane, melting point 168°–178° C. (maleate)
bh) exo-6-thien-2-yl-3-azabicyclo[3.2.0]heptane, melting point 180°–182°C. (hydrochloride)
bi) exo-6-thien-2-yl-3-azabicyclo[3.2.0]heptane, melting point 143°–145° C. (hydrochloride)
bk) exo-6-(5-chlorothien-2-yl)-3-azabicyclo[3.2.0]heptane, melting point 156°–157° C. (maleate)
bl) exo-6-pyrrol-2-yl-3-azabicyclo[3.2.0]heptane
bm) exo-6-pyrid-4-yl-3-azabicyclo[3.2.0]heptane
bn) exo-6-pyrid-2-yl-3-azabicyclo[3.2.0]heptane

B PREPARATION OF THE FINAL PRODUCTS

EXAMPLE 1

6-β-[exo-6-p-Fluorophenyl-3-azabicyclo[3.2.0]heptan-3-yl]ethyl-7-methyl-5H-thiazolo[3,2-a]pyrimidin-5-one dihydrochloride

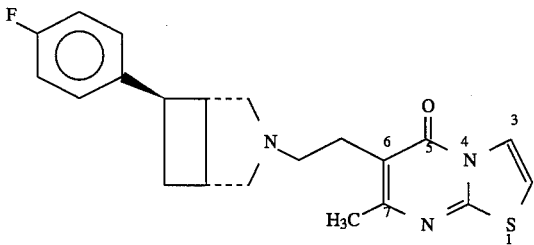

3.6 g (26 mM [sic]) of 6-(2-chloroethyl)-7-methyl-5H-thiazolo[3,2-a]pyrimidin-5-one and 5.6 g (40 mM [sic]) of finely powdered calcium carbonate and 0.5 g of potassium iodide were added to 2.5 g (13.1 mM [sic]) of exo-6-p-fluorophenyl-3-azabicyclo[3.2.0]heptane in 40 ml of xylene, and the mixture was refluxed while stirring vigorously for 11 h.

After cooling, the mixture was concentrated in a rotary evaporator, and the residue was partitioned between methylene chloride and water.

The aqueous phase was extracted twice with methylene chloride, and then the organic phase was dried with sodium sulfate and concentrated. The crude product (7.7 g) was purified by column chromatography (silica gel, methylene chloride/methanol 96/4).

The free base (3.5 g) was taken up in 150 ml of ether, the mixture was filtered to remove insolubles, and excess ethereal hydrochloric acid was added to the solution. The solid was then filtered off with suction under nitrogen in the cold, washed with a large amount of ether and dried on the funnel under nitrogen. 3.5 g (60%) of product ×2 HCl, melting point 222°–224° C., were isolated. The maleate melts at 133°–135° C.

The following can be prepared in a similar way:

1a. (+)-6-β-[exo-6-p-fluorophenyl-3-azabicyclo[3.2.0]heptan-3-yl]ethyl-7-methyl-5H-thiazolo[3,2-a]pyrimidin-5-one maleate, melting point 158°–160° C., $[\alpha]_D 32$ +56.2° (EtOH)

1b. (−)-6-β-[exo-6-p-fluorophenyl-3-azabicyclo[3.2.0]heptan-3-yl]ethyl-7-methyl-5H-thiazolo[3,2-a]pyrimidin-5-one maleate, melting point 147°–149° C., $[\alpha]_D = -52.8°$ (EtOH)

2. 6-β-[exo-6-phenyl-3-azabicyclo[3.2.0]heptan-3-yl]-ethyl-7-methyl-5H-thiazolo[3,2-a]pyrimidin-5-one, melting point 167°–168° C. (maleate)

3. 6-β-[exo-6,7-diphenyl-3-azabicyclo[3.2.0]heptan-3-yl]ethyl-7-methyl-5H-thiazolo[3,2-a]pyrimidin-5-one, melting point 154°–156° C.

4. 6-β-[exo-6,7-bis-(p-fluorophenyl-3-azabicyclo[3.2.0]heptan-3-yl]ethyl-7-methyl-5H-thiazolo-[3,2-a]pyrimidin-5-one 5. 6-β-[exo-6-m-chlorophenyl-3-azabicyclo[3.2.0]heptan-3-yl]ethyl-7-methyl-5H-thiazolo[3,2-a]pyrimidin-5-one, melting point 162°–164° C. (maleate)

6. 6-β-[exo-6-m-methoxyphenyl-3-azabicyclo[3.2.0]heptan-3-yl]ethyl-7-methyl-5H-thiazolo[3,2-a]-pyrimidin-5-one, melting point 149°–152° C. (maleate)

7. 6-β-[exo-6-m-hydroxyphenyl-3-azabicyclo[3.2.0]heptan-3-yl]ethyl-7-methyl-5H-thiazolo[3,2-a]-pyrimidin- 5-one (see also Example 49), melting point 76°–78° C.

8. 6-β-[exo-6-p-aminophenyl-3-azabicyclo[3.2.0]heptan-3-yl]ethyl-7-methyl-5H-thiazolo[3,2-a]pyrimidin-5-one (see also Example 50)

9. 6-β-[exo-6-p-chlorophenyl-3-azabicyclo[3.2.0]heptan-3-yl]ethyl-7-methyl-5H-thiazolo[3,2-a]pyrimidin-5-one, melting point 155°–157° C. (maleate)

10. 6-β-[exo-6-p-methoxyphenyl-3-azabicyclo[3.2.0]heptan-3-yl]ethyl-7-methyl-5H-thiazolo[3,2-a]-pyrimidin-5-one, melting point 168°–170° C. (maleate)

11. 6-β-[exo-6-p-nitrophenyl-3-azabicyclo[3.2.0]heptan-3-yl]ethyl-7-methyl-5H-thiazolo[3,2-a]pyrimidin-5-one 12. 6-β-[exo-6-m-fluorophenyl-3-azabicyclo[3.2.0]heptan-3-yl]ethyl-7-methyl-5H-thiazolo[3,2-a]pyrimidin-5-one 13. 6-β-[exo-6-p-hydroxyphenyl-3-azabicyclo[3.2.0]heptan-3-yl]ethyl-7-methyl-5H-thiazolo[3,2-a]-pyrimidin-5-one (see also Example 49)

14. 6-β-[exo-6-p-trifluoromethylphenyl-3-azabicyclo[3.2.0]heptan-3-yl]ethyl-7-methyl-5H-thiazolo[3,2-a]pyrimidin-5-one, melting point 187°–189° C. (maleate)

15. 6-β-[exo-6-(p-t-butylphenyl)-3-azabicyclo[3.2.0]heptan- 3-yl]ethyl-7-methyl-5H-thiazolo[3,2-a]pyrimidin-5-one, decomposition point 207°–209° C. (maleate)

16. 6-β-[endo-6-(p-t-butylphenyl)-3-azabicyclo[3.2.0]heptan-3-yl]ethyl-7-methyl-5H-thiazolo[3,2-a]pyr-imidin-5-one, melting point 131°–133° C.

17. 6-β-[exo-6-(3,4-dichlorophenyl)-3-azabicyclo[3.2.0]heptan- 3-yl]ethyl-7-methyl-5H-thiazolo[3,2-a]pyrimidin- 5-one 18. 6-β-[exo-6-(3,4-dimethoxyphenyl)-3-azabicyclo[3.2.0]heptan-3-yl]ethyl-7-methyl-5H-thiazolo[3,2-a]pyrimidin-5-one, decomposition point 210°–212° C. (dihydrochloride)

19. 6-β-[exo-6-p-cyanophenyl-3-azabicyclo[3.2.0]heptan-3-yl]ethyl-7-methyl-5H-thiazolo[3,2-a]pyrimidin-5-one, melting point 130°–132° C.

20. 6-β-[exo-6-(3,4-dihydroxyphenyl)-3-azabicyclo[3.2.0]heptan- 3-yl]ethyl-7-methyl-5H-thiazolo[3,2-a]pyrimidin- 5-one (see also Example 49)

21. 6-β-[exo-6-(o-fluorophenyl)-3-azabicyclo[3.2.0]heptan-3-yl]ethyl-7-methyl-5H-thiazolo[3,2-a]pyrimidin- 5-one, melting point 164°–165° C. (maleate)

22. 6-β-[exo-6-thien-3-yl-3-azabicyclo[3.2.0]heptan-3-yl]ethyl-7-methyl-5H-thiazolo[3,2-a]pyrimidin-5-one 23. 6-β-[exo-6-(5-chlorothien-2-yl)-3-azabicyclo[3.2.0]heptan- 3-yl]ethyl-7-methyl-5H-thiazolo[3,2-a]pyrimidin-5-one 24. 6-β-[exo-6-pyrrol-2-yl-3-azabicyclo[3.2.0]heptan-3-yl]ethyl-7-methyl-5H-thiazolo[3,2-a]pyrimidin-5-one 25. 6-β-[exo-6-pyrid-4-yl-3-azabicyclo[3.2.0]heptan-3-yl]ethyl-7-methyl-5H-thiazolo[3,2-a]pyrimidin-5-one 26. 6-β-[exo-6-pyrid-3-yl-3-azabicyclo[3.2.0]heptan-3-yl]ethyl-7-methyl-5H-thiazolo[3,2-a]pyrimidin-5-one 27. 6-β-[exo-6-p-fluorophenyl-3-azabicyclo[3.2.0]heptan-3-yl]ethyl-7-methyl-2,3-dihydro-5H-thiazolo[3,2-a]pyrimidin- 5-one, melting point 253°–255° C.

28. 6-β-[exo-6-m-chlorophenyl-3-azabicyclo[3.2.0]heptan-3-yl]ethyl-7-methyl-2,3-dihydro-5H-thiazolo[3,2-a]pyrimidin- 5-one 29. 6-β-[exo-6-p-fluorophenyl-3-azabicyclo[3.2.0]heptan-3-yl]ethyl-2,3,7-trimethyl-5H-thiazolo[3,2-a]pyrimidin-5-one 30. 6-β-[exo-6-p-fluorophenyl-3-azabicyclo[3.2.0]heptan-3-yl]ethyl-5H-thiazolo[3,2-a]pyrimidin-5-one, melting point 164°–166° C. (dihydrochloride ×H$_2$O)
31. 6-β-[exo-6-p-phenylphenyl-3-azabicyclo[3.2.0]heptan-3-yl]ethyl-5H-thiazolo[3,2-a]pyrimidin-5-one.

EXAMPLE 32

7-β-[exo-6-p-Fluorophenyl 1-3-azabicyclo[3.2.0]heptan-3-yl]ethyl-8-methyl-3,4-dihydro-2H,6H-pyrimido[2,1-b][1,3]-thiazin-6-one dihydrochloride

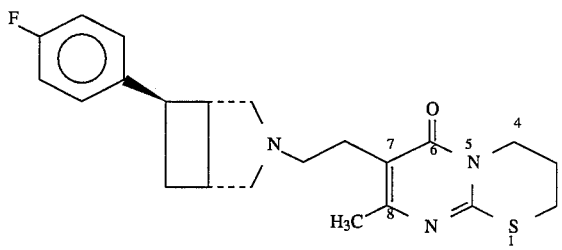

3.3 g (13.6 mM [sic]) of 7-chloroethyl-8-methyl-2H,6H-pyrimido[2,1-b][1,3]thiazin-6-one and 5.0 g (36 mM [sic]) of finely powdered potassium carbonate and 0.5 g of potassium iodide were added to 2.5 g (13.1 mM [sic]) of exo-6-p-fluorophenyl-3-azabicyclo[3.2.0]heptane in 40 ml of xylene, and the mixture was refluxed while stirring vigorously for 12 h.

After cooling, the mixture was concentrated in a rotary evaporator, and the residue was partitioned between methylene chloride and water.

The aqueous phase was then extracted twice with methylene chloride, and the organic phase was dried with sodium sulfate and concentrated. The crude product (5.6 g) was purified by column chromatography (silica gel, methylene chloride/methanol 93/7).

The free base was taken up in 200 ml of ether, the mixture was filtered to remove insolubles, and excess ethereal hydrochloric acid was added to the solution. The solid was then filtered off with suction under nitrogen in the cold, washed with a large amount of ether and dried on the funnel under nitrogen. 3.2 g (52%) of product ×2 HCl, melting point 120°–121° C., were isolated.

The following can be prepared in a similar way:
33. 7-β-[exo-6-phenyl-3-azabicyclo[3.2.0]heptan-3-yl] ethyl-8-methyl-3,4-dihydro-2H,6H-pyrimido[2,1-b][1,3] thiazin-6-one,
34. 7-β-[exo-6-m-chlorophenyl-3-azabicyclo[3.2.0]heptan-3-yl]ethyl-8-methyl-3,4-dihydro-2H,6H-pyrimido[2,1-b][1,3]-thiazin-6-one,
35. 7-β-[exo-6-p-chlorophenyl-3-azabicyclo[3.2.0]heptan-3-yl]ethyl-8-methyl-3,4-dihydro-2H,6H-pyrimido[2,1-b][1,3]thiazin-6-one,
36. 7-β-[exo-6-p-methoxyphenyl-3-azabicyclo[3.2.0]heptan- 3-yl]ethyl-8-methyl-3,4-dihydro-2H,6H-pyrimido[2,1-b][1,3]thiazin-6-one,
37. 7-β-[exo-6-m-hydroxyphenyl-3-azabicyclo[3.2.0]heptan- 3-yl]ethyl-8-methyl-3,4-dihydro-2H,6H-pyrimido[2,1-b][1,3]thiazin-6-one (see also Example 49),
38. 3-β-[exo-6-p-fluorophenyl-3-azabicyclo[3.2.0]heptan-3-yl]ethyl-2,4(1H,3H)quinazolinedione, melting point 158°–160° C.,
38a. (+)-3-β-[exo-6-p-fluorophenyl-3-azabicyclo[3.2.0]heptan- 3-yl]ethyl-2,4(1H,3H)quinazolinedione, melting point 160°–162° C., [α]$_D$=+88.6° (CH$_2$Cl$_2$)
38b. (−)-3-β-[exo-6-p-fluorophenyl-3-azabicyclo[3.2.0] heptan- 3-yl]ethyl-2,4(1H,3H)quinazolinedione, melting point 161°–162° C., [α]$_D$=−87.5° (CH$_2$Cl$_2$)
39. 3-β-[3-azabicyclo[3.2.0]heptan-3-yl]ethyl-2,4-(1H,3H)-quinazolinedione, melting point 158°–160° C.,
40. 3-β-[exo-6-phenyl-3-azabicyclo[3.2.0]heptan-3-yl] ethyl- 2,4(1H,3H)-quinazolinedione, melting point 144°–146° C.,
41. 3-β-[exo-6-m-fluorophenyl-3-azabicyclo[3.2.0]heptan-3-yl]ethyl-2,4(1H,3H)-quinazolinedione,
42. 3-β-[exo-6-p-cyanophenyl-3-azabicyclo[3.2.0]heptan-3-yl]ethyl-2,4(1H,3H)-quinazolinedione, melting point 230°–232° C.,
43. 3-β-[exo-6-m-chlorophenyl-3-azabicyclo[3.2.0]heptan-3-yl]ethyl-2,4(1H,3H)-quinazolinedione, melting point 183°–185° C.,
44. 3-β-[exo-6-p-hydroxyphenyl-3-azabicyclo[3.2.0]heptan- 3-yl]ethyl-2,4(1H,3H)-quinazolinedione, melting point 220°–223° C. (see also Example 49),
45. 3-β-[exo-6-p-chlorophenyl-3-azabicyclo[3.2.0]heptan-3-yl]ethyl-2,4(1H,3H)-quinazolinedione, melting point 187°–189° C.,
46. 3-β-[exo-6-m-methoxyphenyl-3-azabicyclo[3.2.0]heptan- 3-yl]ethyl-2,4(1H,3H)-quinazolinedione, melting point 113°–115° C.,
47. 3-β-[exo-6-p-nitrophenyl-3-azabicyclo[3.2.0]heptan-3-yl]ethyl-2,4(1H,3H)-quinazolinedione, melting point 209°–211° C.,
48. 3-β-[endo-6-p-nitrophenyl-3-azabicyclo[3.2.0]heptan-3-yl]ethyl-2,4(1H,3H)-quinazolinedione, melting point 212°–214° C.

EXAMPLE 49

3-β-[exo-6-m-Hydroxyphenyl-3-azabicyclo[3.2.0]heptan-3-yl]ethyl-2,4(1H,3H)-quinazolinedione

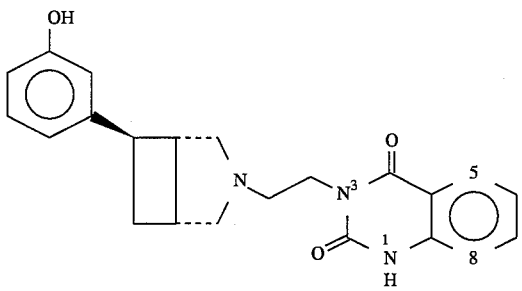

28.5 ml (28.5 mM [sic]) of boron tribromide (1M solution in methylene chloride) were added dropwise to 4.6 g (11.8 mM [sic]) of 3-β-[exo-6-m-methoxyphenyl-3-azabicyclo [3.2.0]hept-3-yl]ethyl-2,4(1H,3H)-quinazolinedione in 120 ml of methylene chloride at room temperature, and the mixture was stirred overnight. After cooling, 100 ml of 2N sodium hydroxide solution were added, the organic phase was separated off, and the aqueous phase was extracted with methylene chloride. Drying and concentration resulted in 4.7 g of crude product which was purified by column chromatography (silica gel, methylene chloride/methanol 96/4). Yield: 2.8 g (61%), melting point 149°–151° C. (hydrochloride).

EXAMPLE 50

3-β-[exo-6-p-Aminophenyl-3-azabicyclo[3.2.0]heptan-3-yl]ethyl-2,4(1H,3H)-quinazolinedione 16.3 g (40.1 mM [sic]) of 3-β-[exo-6-p-nitrophenyl-3-azabicyclo[3.2.0]hept-3-yl]ethyl-2,4(1H,3H)-quinazolinedione were dissolved in 300 ml of glacial acetic acid, 1.7 g of palladium on carbon (10%) were added, and the mixture was hydrogenated at room temperature under atmospheric pressure for 4 h. The catalyst was filtered off with suction, the mother liquor was concentrated, the residue was taken up in 400 ml of water, the solution was made alkaline by stirring with concentrated ammonia, and the precipitated solid was filtered off with suction, washing with water. The crude product (15.3 g) was purified by column chromatography (silica gel, methylene chloride/methanol 95/5). Yield: 12.4 g (76%) with melting point 196°–198° C.

EXAMPLE 51

3-β-[exo-6-p-Iodophenyl-3-azabicyclo[3.2.0]heptan-3-yl]ethyl-2,4(1H,3H)-quinazolinedione 5.6 g (14.9 mM [sic]) of 3-β-[exo-6-p-aminophenyl-3-azabicyclo[3.2.0]hept-3-yl]ethyl-2,4(1H,3H)-quinozalinedione were dissolved in 100 ml of 50% concentrated hydrochloric acid At 0°–5° C., a solution of 1.05 g (15.0 mM[sic]) of sodium nitrite in 6 ml of water was added dropwise, and the mixture was then stirred at the same temperature for 20 min. Subsequently a solution of 2.5 g (15.0 mM [sic]) of potassium iodide in 12 ml of water was added, the ice bath was removed, and the mixture was slowly heated while stirring vigorously to 85°–90° C. After 40 min, the mixture was allowed to cool, ice/water were added, the mixture was made alkaline with concentrated ammonia, 300 ml of methylene chloride were added, and the mixture was then stirred vigorously. After phase separation, the aqueous phase was extracted with methylene chloride, and the combined organic phases were dried and concentrated. The crude product (6.0 g) was purified by column chromatography (silica gel, methylene chloride/methanol 95/5). Yield: 3.2 g (57%), melting point 162°–164° C.

52. 3-β-[exo-6-p-trifluormethylphenyl-3-azabicyclo[3.2.0]heptan-3-yl]ethyl-2,4(1H,3H)-quinazolinedione, melting point 190°–192° C.,
53. 3-β-[exo-6-(3,4-dichlorophenyl)-3-azabicyclo[3.2.0]heptan-3-yl]ethyl-2,4(1H,3H)-quinazolinedione,
54. 3-β-[exo-6-(3,4-dihydroxyphenyl)-3-azabicyclo[3.2.0]heptan-3-yl]ethyl-2,4(1H,3H)-quinazolinedione (as Example 49),
55. 3-β-[exo-6-(3,5-dichlorophenyl)-3-azabicyclo[3.2.0]heptan-3-yl]ethyl-2,4(1H,3H)-quinazolinedione, melting point 189°–192° C.,
56. 3-β-[exo-6-o-fluorophenyl-3-azabicyclo[3.2.0]heptan-3-yl]ethyl-2,4(1H,3H)-quinazolinedione,
57. 3-β-[exo-6-p-fluorophenyl-3-azabicyclo[3.2.0]heptan-3-yl]ethyl-8-methyl-2,4(1H,3H)-quinazolinedione, melting point 170°–173° C.,
58. 3-β-[exo-6-p-fluorophenyl-3-azabicyclo[3.2.0]heptan-3-yl]ethyl-7-chloro-2,4(1H,3H)-quinazolinedione, melting point 214°–216° C.,
59. 3-β-[exo-6-p-fluorophenyl-3-azabicyclo[3.2.0]heptan-3-yl]ethyl-7-fluoro-2,4(1H,3H)-quinazolinedione,
60. 3-β-[exo-6-p-fluorophenyl-3-azabicyclo[3.2.0]heptan-3-yl]ethyl-5-chloro-2,4(1H,3H)-quinazolinedione, melting point
61. 3-β-[exo-6-p-fluorophenyl-3-azabicyclo[3.2.0]heptan-3-yl]ethyl-6-fluoro-2,4(1H,3H)-quinazolinedione, melting point 186°–188° C.,
62. 3-β-[exo-6-p-fluorophenyl-3-azabicyclo[3.2.0]heptan-3-yl]ethyl-6-methyl-2,4(1H,3H)-quinazolinedione, melting point 166°–168° C.,
63. 3-β-[exo-6-p-fluorophenyl-3-azabicyclo[3.2.0]heptan-3-yl]ethyl-8-methoxy-2,4(1H,3H)-quinazolinedione,
64. 3-β-[exo-6-p-fluorophenyl-3-azabicyclo[3.2.0]heptan-3-yl]ethyl-6-trifluoromethyl-2,4(1H,3H)-quinazolinedione,
65. 3-β-[exo-6-p-fluorophenyl-3-azabicyclo[3.2.0]heptan-3-yl]ethyl-7-nitro-2,4(1H,3H)-quinazolinedione,
66. 3-β-[exo-6-p-fluorophenyl-3-azabicyclo[3.2.0]heptan-3-yl]ethyl-6-nitro-2,4(1H,3H)-quinazolinedione,
67. 3-β-[exo-6-p-fluorophenyl-3-azabicyclo[3.2.0]heptan-3-yl]ethyl-7-amino-2,4(1H,3H)-quinazolinedione,
68. 3-β-[exo-6-p-fluorophenyl-3-azabicyclo[3.2.0]heptan-3-yl]ethyl-6-amino-2,4(1H,3H)-quinazolinedione,
69. 3-β-[exo-6-p-fluorophenyl-3-azabicyclo[3.2.0]heptan-3-yl]ethyl-6-hydroxy-2,4(1H,3H)-quinazolinedione,
70. 3-β-[exo-6-p-fluorophenyl-3-azabicyclo[3.2.0]heptan-3-yl]ethyl-5-chloro-2,4(1H,3H)-quinazolinedione, melting point 194°–196° C. (maleate),
71. 3-β-[exo-6-p-fluorophenyl-3-azabicyclo[3.2.0]heptan-3-yl]ethyl-6,7-dimethoxy-2,4(1H,3H)-quinazolinedione, melting point 203°–205° C.,
72. 3-β-[exo-6-p-fluorophenyl-3-azabicyclo[3.2.0]heptan-3-yl]ethyl-6,8-dichloro-2,4(1H,3H)-quinazolinedione,
73. 3-β-[exo-6-p-fluorophenyl-3-azabicyclo[3.2.0]heptan-3-yl]ethyl-6,7,8-trimethoxy-2,4(1H,3H)-quinazolinedione,
74. 3-β-[exo-6-p-fluorophenyl-3-azabicyclo[3.2.0]heptan-3-yl]ethyl-1-methyl-2,4-(1H,3H)quinazolinedione, melting point 89°–90° C.,
75. 3-β-[exo-6-p-fluorophenyl-3-azabicyclo[3.2.0]heptan-3-yl]ethyl-1-ethyl-2,4(1H,3H)-quinazolinedione, melting point 92°–95° C. (hydrochloride),
76. 3-β-[exo-6-p-fluorophenyl-3-azabicyclo[3.2.0]heptan-3-yl]ethyl-1-allyl-2,4(1H,3H)-quinazolinedione,
77. 3-β-[exo-6-p-fluorophenyl-3-azabicyclo[3.2.0]heptan-3-yl]ethyl-1-benzyl-2,4(1H,3H)-quinazolinedione, melting point 133°–135° C.,
78. 3-γ-[exo-6-p-fluorophenyl-3-azabicyclo[3.2.0]heptan-3-yl]propyl-2,4(1H,3H)quinazolinedione, melting point 75°–77° C.,
79. 3-ε-[exo-6-p-fluorophenyl-3-azabicyclo[3.2.0]heptan-3-yl]butyl-2,4(1H,3H)quinazolinedione,
80. 3-β-[exo-6-(2-thienyl)-3-azabicyclo[3.2.0]heptan-3-yl]ethyl-2,4(1H,3H)quinazolinedione, melting point 171°–173° C.,
81. 3-β-[exo-6-(5-chloro-2-thienyl)-3-azabicyclo[3.2.0]heptan-3-yl]ethyl-2,4(1H,3H)quinazolinedione, decomposition above 176° C.,
82. 3-β-[exo-6-(3-thienyl)-3-azabicyclo[3.2.0]heptan-3-yl]ethyl-2,4(1H,3H)quinazolinedione, melting point 158°–159° C.,
83. 3-β-[exo-6-(3-pyridyl)-3-azabicyclo[3.2.0]heptan-3-yl]ethyl-2,4-(1H,3H)quinazolinedione, decomposition above 84° C.,
84. 3-β-[exo-6-p-fluorophenyl-3-azabicyclo[3.2.0]heptan-3-yl]ethyl-1H-thieno[3,2-d]pyrimidine-2,4-dione, melting point 230°–232° C.,
85. 3-β-[exo-6-p-fluorophenyl-3-azabicyclo[3.2.0]heptan-3-yl]ethyl-1H-thieno[2,3-d]pyrimidine-2,4-dione,
86. 3-β-[exo-6-p-fluorophenyl-3-azabicyclo[3.2.0]heptan-3-yl]ethyl-1H-thieno[3,4-d]pyrimidine-2,4-dione, 87. 3-β-[exo-6-p-fluorophenyl-3-azabicyclo[3.2.0]heptan-3-yl]ethyl-1-methyl-1H,3H-pyrido[2,3-d]pyrimidine-2,4-dione,
88. 3-β-[exo-6-p-fluorophenyl-3-azabicyclo[3.2.0]heptan-3-yl]ethyl-2-methyl-3H-quinazolin-4-one, decomposition above 225° C. (hydrochloride),
89. 3-β-[exo-6-p-fluorophenyl-3-azabicyclo[3.2.0]heptan-3-yl]ethyl-2-methoxy-3H-quinazolin-4-one.

EXAMPLE 90

3-β-[exo-6-p-Fluorophenyl-3-azabicyclo[3.2.0]heptan-3-yl]-ethyl-2-methyl-4H-pyrido[1,2-a]pyrimidin-4-one dihydrochloride

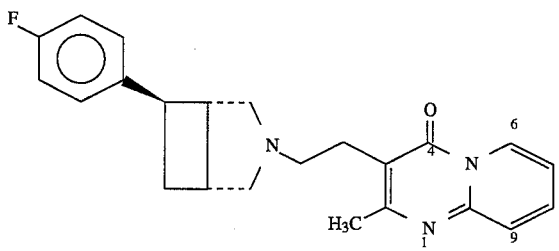

3.8 g (17 mM [sic]) of 3-(2-chloroethyl)-2-methyl-4H-pyrido[1,2-a]pyrimidin-4-one and 4.2 g (30 mM [sic]) of finely powdered potassium carbonate and 0.5 g of potassium iodide were added to 3.0 g (15.7 mM [sic]) of exo-6-p-fluorophenyl-3-azabicyclo[3.2.0]heptane in 60 ml of xylene, and the mixture was refluxed with vigorous stirring for 11 h. After cooling, the mixture was concentrated in a rotary evaporator and the residue was partitioned between methylene chloride and water. The aqueous phase was extracted twice with methylene chloride and then the organic phase was dried with sodium sulfate and concentrated. The crude product (7.8 g) was purified by column chromatography (silica gel, methylene chloride/methanol 94/4). The free base (3.4 g) was taken up in 200 ml of ether, the mixture was filtered to remove insolubles, and excess ethereal hydrochloric acid was added to this solution. The solid was then filtered off with suction under nitrogen in the cold, washed with a large quantity of ether and dried on the funnel under nitrogen. 3.8 g (54%) of product ×2 HCl, melting point >250° C., were isolated.

The following can be prepared in a similar way:
91. 3-β-[exo-6-phenyl-3-azabicyclo[3.2.0]heptan-3-yl]ethyl-2-methyl-4H-pyrido[1,2-a]pyrimidin-4-one,
92. 3-β-[exo-6-m-chlorophenyl-3-azabicyclo[3.2.0]heptan-3-yl]ethyl-2-methyl-4H-pyrido[1,2-a]pyrimidin-4-one,
93. 3-β-[exo-6-m-methoxyphenyl-3-azabicyclo[3.2.0]heptan-3-yl]ethyl-2-methyl-4H-pyrido[1,2-a]-pyrimidin-4-one,
94. 3-β-[exo-6-p-fluorophenyl-3-azabicyclo[3.2.0]heptan-3-yl]ethyl-2,6-dimethyl-4H-pyrido[1,2-a]pyrimidin-4one, melting point 59°–61° C. (dihydrochloride),
95. 3-β-[exo-6-p-fluorophenyl-3-azabicyclo[3.2.0]heptan-3-yl]ethyl-2,7-dimethyl-4H-pyrido[1,2-a]pyrimidin-4one, melting point 247°–249° C. (dihydrochloride),
96. 3-β-[exo-6-p-fluorophenyl-3-azabicyclo[3.2.0]heptan-3-yl]ethyl-2,8-dimethyl-4H-pyrido[1,2-a]pyrimidin-4one, melting point >250° C. (dihydrochloride),
97. 3-β-[exo-6-p-fluorophenyl-3-azabicyclo[3.2.0]heptan-3-yl]ethyl-2,9-dimethyl-4H-pyrido[1,2-a]pyrimidin-4one, decomposition >208° C. (dihydrochloride),
98. 3-β-[exo-6-p-fluorophenyl-3-azabicyclo[3.2.0]heptan-3-yl]ethyl-2,6,8-trimethyl-4H-pyrido[1,2-a]-pyrimidin-4-one, melting point >260° C. (dihydrochloride),
99. 3-β-[exo-6-m-chlorophenyl-3-azabicyclo[3.2.0]heptan-3-yl]ethyl-2,7-dimethyl-4H-pyrido[1,2-a]pyrimidin-4-one, melting point >250° C. (dihydrochloride),
100. 3-β-[exo-6-o-chlorophenyl-3-azabicyclo[3.2.0]heptan-3-yl]ethyl-2,7-dimethyl-4H-pyrido[1,2-a]pyrimidin-4one, melting point 262°–264° C. (dihydrochloride),
101. 3-β-[exo-6-phenyl-3-azabicyclo[3.2.0]heptan-3-yl]ethyl-2,8-dimethyl-4H-pyrido[1,2-a]pyrimidin-4-one, melting point >250° C. (dihydrochloride),
102. 3-β-[exo-6-m-chlorophenyl-3-azabicyclo[3.2.0]heptan-3-yl]ethyl-2,9-dimethyl-4H-pyrido[1,2-a]pyrimidin-4-one, decomposition >213° C. (dihydrochloride),
103. 3-β-[exo-6-(5-chlorothien-2-yl)-3-azabicyclo[3.2.0]heptan- 3-yl]ethyl-2-methyl-4H-pyrido[1,2-a]-pyrimidin-4-one,
104. 3-β-[exo-6-pyrid-4-yl-3-azabicyclo[3.2.0]heptan-3-yl]ethyl-2-methyl-4H-pyrido[1,2-a]pyrimidin-4-one,
105. 3-βD-[exo-6-p-fluorophenyl-3-azabicyclo[3.2.0]heptan-3-yl]ethyl-6,7,8,9-tetrahydro-2-methyl-4H-pyrido[1,2-a]pyrimidin-4-one, melting point 151°–153° C. (maleate),
106. 3-β-[exo-6-p-chlorophenyl-3-azabicyclo[3.2.0]heptan-3-yl]ethyl-6,7,8,9-tetrahydro-2-methyl-4H-pyrido[1,2-a]pyrimidin-4-one,
107. 3-β-[exo-6-p-methoxyphenyl-3-azabicyclo[3.2.0]heptan- 3-yl]ethyl-6,7,8,9-tetrahydro-2-methyl-4H-pyrido-[1,2-a]pyrimidin-4-one,
108. 3-β-[exo-6-p-fluorophenyl-3-azabicyclo[3.2.0]heptan-3-yl]ethyl-2-methyl-4H-pyrimido[1,2-a]pyrimidin-4-one,
109. 3-β-[exo-6-p-fluorophenyl-3-azabicyclo[3.2.0]heptan-3-yl]ethyl-2-methyl-7-chloro-4H-pyrimido[1,2-a]pyrimidin-4-one,
110. 6-β-[exo-6-p-fluorophenyl-3-azabicyclo[3.2.0]heptan-3-yl]ethyl-7-methyl-1H,5H-imidazo[1,2-a]pyrimidin-4-one,
111. 3-β-[exo-6-p-fluorophenyl-3-azabicyclo[3.2.0]heptan-3-yl]ethyl-2-methyl-7,8-dihydro-4H,6H-pyrrolo[1,2-a]pyrimidin-4-one,
112. 2-[exo-6-p-fluorophenyl-3-azabicyclo[3.2.0]heptan-3-yl]methylbenzimidazole, melting point 166°–168° C.,
113. 1-β-[exo-6-p-fluorophenyl-3-azabicyclo[3.2.0]heptan-3-yl]ethylbenzimidazole, melting point 94°–96° C. (hydrochloride),
114. 1-β-[exo-6-p-fluorophenyl-3-azabicyclo[3.2.0]heptan-3-yl]ethyl-2,3-dihydrobenzimidazol-2-one,
115. 2-[exo-6-m-methoxyphenyl-3-azabicyclo[3.2.0]heptan-3-yl]methylbenzimidazole,
116. 3-β-[exo-6-p-fluorophenyl-3-azabicyclo[3.2.0]heptan-3-yl]ethylindole, melting point 193°–195° C. (hydrochloride),
117. 3-β-2-[exo-6-m-chlorophenyl-3-azabicyclo[3.2.0]heptan- 3-yl]ethylindole,
118. 3-β-[exo-6-phenyl-3-azabicyclo[3.2.0]heptan-3-yl]ethylindole, melting point 104°–105° C. (hydrochloride),
119. 3-β-[exo-6-m-methoxyphenyl-3-azabicyclo[3.2.0]heptan- 3-yl]ethylindole,
120. 2-[exo-6-p-fluorophenyl-3-azabicyclo[3.2.0]heptan-3-yl]methyl-3,4-dihydro-4-quinazolinone, melting point 152°–154° C.,
121. 2-[exo-6-p-fluorophenyl-3-azabicyclo[3.2.0]heptan-3-yl]methyl-3,4-dihydro-4-quinazolinethione,
122. 2-[exo-6-phenyl-3-azabicyclo[3.2.0]heptan-3-yl]methyl-3,4-dihydro-4-quinazolinone, melting point 147°–149° C., 123. 2-[exo-6-m-chlorophenyl-3-azabicyclo[3.2.0]heptan-3-yl]methyl-3,4-dihydro-4-quinazolinone,
124. 2-[exo-6-o-methoxyphenyl-3-azabicyclo[3.2.0]heptan-3-yl]methyl-3,4-dihydro-4-quinazolinone,
125. 2-[exo-6-p-fluorophenyl-3-azabicyclo[3.2.0]heptan-3-yl]methyl-4-hydroxy-6-methylpyrimidine, melting point 174°–175° C.,
126. 6-[exo-6-p-fluorophenyl-3-azabicyclo[3.2.0]heptan-3-yl]methyl-2-methyl-4-hydroxypyrimidine, melting point 147°–149° C. (dihydrochloride),
127. 6-[exo-6-p-fluorophenyl-3-azabicyclo[3.2.0]heptan-3-yl]methyluracil, melting point 201°–203° C.,
128. 6-[exo-6-phenyl-3-azabicyclo[3.2.0]heptan-3-yl]methyluracil, melting point 183°–184° C.,
129. 6-[exo-6-p-fluorophenyl-3-azabicyclo[3.2.0]heptan-3-yl]-1,2,3,4-tetrahydro-1,3-dimethyl-2,4-dioxopyrimidine, melting point 108°–110° C. (hydrochloride),
130. 5-β-[exo-6-p-fluorophenyl-3-azabicyclo[3.2.0]heptan-3-yl]ethyl-1,2,3,4-tetrahydro-6-methyl-2,4-dioxopyrimidine, melting point 197°–199° C.,
131. 5-β-[exo-6-p-fluorophenyl-3-azabicyclo[3.2.0]heptan-3-yl]ethyl-1,2,3,4-tetrahydro-1,6-dimethyl-2,4-dioxopyrimidine, melting point 186°–188° C.,
132. 5-β-[exo-6-p-fluorophenyl-3-azabicyclo[3.2.0]heptan-3-yl]ethyl-1,2,3,4-tetrahydro-3,6-dimethyl-2,4-dioxopyrimidine,
133. 5-β-[exo-6-p-fluorophenyl-3-azabicyclo[3.2.0]heptan-3-yl]ethyl-1,2,3,4-tetrahydro-3,6-dimethyl-2,4-dithiopyrimidine,
134. 5-β-[exo-6-p-fluorophenyl-3-azabicyclo[3.2.0]heptan-3-yl]ethyl-1,2,3,4-tetrahydro-1,3,6-trimethyl-2,4-dioxopyrimidine, melting point 90°–93° C. (hydrochloride),
135. 5-β-[exo-6-p-fluorophenyl-3-azabicyclo[3.2.0]heptan-3-yl ethyl-2-thiomethyl-6-methyl-4(3H)-pyrimidinone,
136. 5-β-[exo-6-p-fluorophenyl-3-azabicyclo[3.2.0]heptan-3-yl]ethyl-2-mercapto-6-methyl-4(3H)-pyrimidinone,
137. 5-β-[exo-6-p-fluorophenyl-3-azabicyclo[3.2.0]heptan-3-yl]ethyl-2-thiomethyl-3,6-dimethyl-4(3H)-pyrimidinone,
138. 5-β-[exo-6-p-fluorophenyl-3-azabicyclo[3.2.0]heptan-3-yl]ethyl-1,2,3,4-tetrahydro-6-amino-1-methyl-2,4-dioxopyrimidine
139. 5-β-[exo-6-p-fluorophenyl-3-azabicyclo[3.2.0]heptan-3-yl]ethyl-2-amino-6-methyl-4(3H)-pyrimidinone,
140. 5-β-[exo-6-p-fluorophenyl-3-azabicyclo[3.2.0]heptan-3-yl]ethyl-2-amino-3,6-dimethyl-4(3H)-pyrimidinone, melting point 78°–80° C.,
141. 5-β-[exo-6-p-fluorophenyl-3-azabicyclo[3.2.0]heptan-3-yl]ethyl-2-methylamino-3,6-dimethyl-4(3H)-pyrimidinone, melting point 163°–165° C. (dihydrochloride),
142. 5-β-[exo-6-p-fluorophenyl-3-azabicyclo[3.2.0]heptan-3-yl]ethyl-2-dimethylamino-4(3H)-pyrimidinone,
143. 5-β-[exo-6-p-fluorophenyl-3-azabicyclo[3.2.0]heptan-3-yl]ethyl-2-methylamino-3-ethyl-6-methyl-4(3H)-pyrimidinone,
144. 5-β-[exo-6-p-fluorophenyl-3-azabicyclo[3.2.0]heptan-3-yl]ethyl-2-amino-3-ethyl-6-methyl-4(3H)-pyrimidinone, melting point 77°–80° C. (hydrochloride),
145. 5-β-[exo-6-p-fluorophenyl-3-azabicyclo[3.2.0]heptan-3-yl]ethyl-2-ethylamino-3,6-dimethyl-4(3H)-pyrimidinone,
146. 5-β-[exo-6-p-fluorophenyl-3-azabicyclo[3.2.0]heptan-3-yl]ethyl-2-n-propylamino-3,6-dimethyl-4(3H)-pyrimidinone,
147. 5-β-[exo-6-p-chlorophenyl-3-azabicyclo[3.2.0]heptan-3-yl]ethyl-2-methylamino-3,6-dimethyl-4(3H)-pyrimidinone, decomposition above 144° C. (dihydrochloride ×2 H$_2$O),
148. 5-β-[exo-6-m-chlorophenyl-3-azabicyclo[3.2.0]heptan-3-yl]ethyl-2-methylamino-3,6-dimethyl-4(3H)-pyrimidinone, melting point 147°–149° C. (dihydrochloride),
149. 5-β-[exo-6-o-fluorophenyl-3-azabicyclo[3.2.0]heptan-3-yl]ethyl-2-methylamino-3,6-dimethyl-4(3H)-pyrimidinone, melting point 173°–175° C. (dihydrochloride),
150. 5-β-[exo-6-p-trifluoromethylphenyl-3-azabicyclo[3.2.0]heptan-3-yl]ethyl-2-methylamino-3,6-dimethyl-4(3H)-pyrimidinone,
151. 5-β-[exo-6-p-cyanophenyl-3-azabicyclo[3.2.0]heptan-3-yl]ethyl-2-methylamino-3,6-dimethyl-4(3H)-pyrimidinone,
152. 5-β-[exo-6-m-fluorophenyl-3-azabicyclo[3.2.0]heptan-3-yl]ethyl-2-methylamino-3,6-dimethyl-4(3H)-pyrimidinone,
153. 5-β-[exo-6-p-fluorophenyl-3-azabicyclo[3.2.0]heptan-3-yl]ethyl-2-methylamino-4-methoxy-6-methylpyrimidine.

We claim:

1. An N-substituted 3-azabicyclo[3.2.0]heptane derivative of the formula I where $R^1$ is phenyl, pyridyl, thienyl or pyrrole, each of which is unsubstituted or mono- or disubstituted by halogen, $C_1$–$C_4$-alkyl, trifluoromethyl, hydroxyl, $C_1$–$C_4$-alkoxy, amino, monomethylamino, dimethylamino, cyano or nitro, $R^2$ is hydrogen or phenyl which is unsubstituted or substituted by halogen, methoxy, hydroxyl or amino, n is 0, 1, 2, 3 or 4, $R^3$ is hydrogen, hydroxyl, $C_1$–$C_4$alkyl or $C_1$–$C_4$-alkoxy, or together with the adjacent carbon atom is C=O or C=S, X and Y are each C, CH, CH$_2$, NH or $C_1$–$C_4$alkyl-N or N, Z is a direct linkage, CO, CS or CH or CH$_2$ in which one hydrogen can be replaced by hydroxyl, amino, $C_1$–$C_1$-alkoxy or halogen, and A is hydrogen, hydroxyl, amino, mercapto, $C_1$–$C_4$-alkylamino, di-$C_1$–$C_4$-alkylamino, $C_1$–$C_1$-alkylthio or $C_1$–$C_4$-alkoxy, or together with the adjacent carbon atom is C=O, or A is $C_3$–$C_4$-alkylene which is attached to Y and which can contain one or two non-cumulative double bonds and in which one CH or CH$_2$ can be replaced by N, S, NH or N—CH$_3$, and where the ring can be either monosubstituted by fluorine, chlorine, methyl, methoxy, nitro or amino or, in the case of a benzene ring, mono-, di- or trisubstituted by fluorine, chlorine, methyl, trifluoromethyl, nitro, hydroxyl, methoxy, amino, monomethylamino or dimethylamino, and in which the ring on the right in formula I can have $C_1$–$C_4$-alkyl, allyl or benzyl attached to N-1 and can contain 1–3 non-cumulative double bonds, and the salts thereof with physiologically tolerated acids.

* * * * *

UNITED STATES PATENT AND TRADEMARK OFFICE
CERTIFICATE OF CORRECTION

PATENT NO.: 5,475,105

DATED: December 12, 1995

INVENTOR(S): STEINER et al.

It is certified that error appears in the above-identified patent and that said Letters Patent is hereby corrected as shown below:

On the cover page, item [75], second inventor's first name should read --Liliane--.

Column 18, claim 1, lines 46 and 49, " $C_1$-$C_1$- " should read -- $C_1$-$C_4$- --, both instances.

Signed and Sealed this

Twenty-sixth Day of March, 1996

Attest:

BRUCE LEHMAN

Attesting Officer     Commissioner of Patents and Trademarks